(12) United States Patent
Van Beuningen et al.

(10) Patent No.: US 7,473,562 B2
(45) Date of Patent: Jan. 6, 2009

(54) METHOD FOR HIGH-THROUGHPUT INTEGRATED CHEMICAL AND BIOCHEMICAL REACTIONS

(75) Inventors: Marinus Gerardus Johannus Van Beuningen, Oss (NL); Pieter Jacob Boender, Nijmegen (NL)

(73) Assignee: PamGene B.V., Den Bosch (NL)

( * ) Notice: Subject to any disclaimer, the term of this patent is extended or adjusted under 35 U.S.C. 154(b) by 407 days.

(21) Appl. No.: 10/515,665

(22) PCT Filed: Jun. 2, 2003

(86) PCT No.: PCT/EP03/05750

§ 371 (c)(1),
(2), (4) Date: Nov. 23, 2004

(87) PCT Pub. No.: WO03/102234

PCT Pub. Date: Dec. 11, 2003

(65) Prior Publication Data

US 2006/0148095 A1 Jul. 6, 2006

(30) Foreign Application Priority Data

Jun. 3, 2002 (EP) .................................. 02447109

(51) Int. Cl.
*G01N 33/558* (2006.01)
(52) U.S. Cl. .................. 436/514; 435/6; 435/288.4; 435/288.5; 436/164; 436/172; 436/805
(58) Field of Classification Search .................. 435/7.1
See application file for complete search history.

(56) References Cited

U.S. PATENT DOCUMENTS

| 4,318,981 | A | * | 3/1982 | Burd et al. | .................... 435/7.7 |
| 4,777,021 | A | * | 10/1988 | Wertz et al. | .................. 422/101 |
| 5,196,306 | A | * | 3/1993 | Bobrow et al. | ................ 435/7.9 |
| 5,273,718 | A | * | 12/1993 | Skold et al. | .................. 422/101 |
| 6,376,233 | B1 | * | 4/2002 | Wolf et al. | ............... 435/288.4 |
| 2002/0115198 | A1 | * | 8/2002 | Nerenberg et al. | ....... 435/287.2 |

FOREIGN PATENT DOCUMENTS

| WO | WO 95/11755 | 5/1995 |
| WO | WO 99/02266 | 1/1999 |
| WO | WO 00/31304 | 6/2000 |
| WO | WO 01/12846 A1 | 2/2001 |
| WO | WO 01/61054 A2 | 8/2001 |

OTHER PUBLICATIONS

Van Beuningen et al., "Fast and Specific Hybridization Using Low-Through Microarrays on Porous Metal Oxide", Clin. Chem., Am. Assoc. for Clin. Chem., Winston, US, vol. 47, No. 10, Dec. 12, 2001, pp. 1931-1933.

* cited by examiner

*Primary Examiner*—Christopher L Chin
(74) *Attorney, Agent, or Firm*—Amster, Rothstein & Ebenstein LLP

(57) ABSTRACT

The present invention relates to methods for monitoring in a high through-put fashion a multitude of molecular reaction processes, using a substrate, said substrate comprising a plurality of micro-channels, wherein each micro-channel has inlet and outlet open ends on opposing sides of said substrate, and wherein said micro-channels comprise at least one first reaction component, comprising the steps of: (a) contacting said micro-channels of said solid substrate with a sample, said contacting being via said inlet open ends, wherein said sample comprises an analyte, under conditions that allow said analyte to be specifically retained within said micro-channels by said first reaction component; (b) optionally removing excess of sample via said outlet open ends; (c) contacting the retained analyte with at least one second reaction component, said second reaction component being different from said first reaction component as defined in step (a), under conditions that allow a molecular reaction to take place, said reaction producing a signal; (d) detecting said signal and reading-out reaction results;(e) removing second reaction components via said outlet open ends; (f) repeating steps (c) to (e) at least once, wherein said at least one second reaction component as defined in (c) may be changed in composition; and, final detecting and reading-out of reaction results. The present invention also relates to the uses thereof as well as to microarrays and kits for performing said methods of the invention.

25 Claims, 7 Drawing Sheets

| Ref | B1 | D1 | G10-B1 |
|---|---|---|---|
| A1 | B2 | G10-A1 | G10-B2 |
| A2 | B3 | G10-A2 | G10-B3 |
| A3 | C1 | G10-A3 | NC |

METHOD FOR HIGH-THROUGHPUT INTEGRATED CHEMICAL AND BIOCHEMICAL REACTIONS

This application is a U.S. National Phase of PCT Application No. PCT/EPO3/05750, filed Jun. 2, 2003 and claims priority to European Application No. 02447109.6, filed Jun. 3, 2002.

FIELD OF THE INVENTION

The present invention relates to a method for performing high throughput parallel small-scale reactions. In particular, the instant disclosure pertains to multiple simultaneous chemical and biochemical molecular micro-reactions.

BACKGROUND OF THE INVENTION

Reaction processes such as chemical and biochemical reactions between two or more molecules in vitro, are frequently carried out within a chamber or container. Such chambers, or reaction vessels, are commonly made of glass or plastic and include, for example, test tubes, micro-centrifuge tubes, capillary tubes and microtiter plates.

These processes commonly involve frequent manual handling of samples like, for instance, the transfer of liquids between containers by pipetting, mixing, centrifugation, incubation, washing and precipitation, just to mention a few procedures. Experimental work is accordingly very time consuming and labour intensive.

Additionally, a general characteristic of methods in, for example, molecular biology is that some of the reagents are available only in small amounts or are very expensive, and therefore in most cases only very small volumes, usually in the µl range, of reagents and reaction mixtures are handled in each step of such a method. Reaction chambers currently in use, however, are not amenable for use with volumes below one microliter, due to, e.g., evaporative losses of the reaction solution.

A solution is provided by the miniaturization of those reactions. For example, WO 01/61054 discloses apparatus and methods for parallel processing of micro-volume liquid reactions.

WO 01/12846 in name of PamGene BV relates to the preparation of metal oxide supports loaded with biomolecules.

WO 99/02266 in name of AKZO NOBEL NV relates to a device for performing an assay, a method for manufacturing said device, and use of a membrane in the manufacture of said device.

WO 00/31304 in name of The Perkin Elmer Corporation relates to methods and apparatus for flow-through hybridization.

WO 95/11755 in name of Houston Advanced Research Center relates to microfabricated, flowthrough porous apparatus for discrete detection of binding reactions.

Van Beuningen et al. (2001 Clinical Chemistry 47: 1931-1933) relates to a fast and specific hybridization using flow-through microarrays on porous metal oxide.

However, neither of the above cited prior art documents relates to performing and monitoring successive reactions.

As will be appreciated in the art, there is a continuous need for improved methods and apparatuses suitable for micro-volume reactions. Therefore the present invention aims to provide an integrated high-throughput method for miniaturized molecular reaction processes.

SUMMARY OF THE INVENTION

Disclosed herein are methods for conducting multiple simultaneous micro-volume chemical and biochemical reactions in an array format. Said format comprises an array of reaction chambers constituted out of micropores through a porous substrate.

Accordingly, the present invention provides a method for monitoring in a high through-put fashion a multitude of molecular reaction processes, using a substrate, said substrate comprising a plurality of micro-channels, wherein each micro-channel has inlet and outlet open ends on opposing sides of said substrate, and wherein said micro-channels comprise at least one first reaction component, comprising the steps of:

(a) contacting said micro-channels of said solid substrate with a sample, said contacting being via said inlet open ends, wherein said sample comprises an analyte, under conditions that allow said analyte to be specifically retained within said micro-channels by said first reaction component;

(b) optionally removing excess of sample via said outlet open ends;

(c) contacting the retained analyte with at least one second reaction component, said second reaction component being different from said first reaction component as defined in step (a), under conditions that allow a molecular reaction to take place, said reaction producing a signal;

(d) detecting said signal and reading-out reaction results;

(e) removing second reaction components via said outlet open ends;

(f) repeating steps (c) to (e) at least once, wherein said at least one second reaction component as defined in (c) may be changed in composition; and, (g) final detecting and reading-out of reaction results.

The miniaturized dimensions of the arrayed reaction chambers allow for highly reduced reagents volumes, short reaction times and fast analysis. The provision of inlet and outlet open ends further allows the abolishment of, e.g., enzymatic degradation steps, thus improving cost-effectiveness of the reactions.

Additional features and advantages of the invention will be set forth in the detailed description which follows, and in part will be apparent from the description, or may be learned by practice of the invention. The objectives and other advantages of the invention will be realized and attained by the process particularly pointed out in the written description and appended claims.

DETAILED DESCRIPTION OF THE INVENTION

The present invention relates in particular to integrated miniaturized molecular reactions.

In the present specification and the appended claims, the singular forms "a", "an", and "the" include plural references unless the context clearly dictates otherwise. Unless defined otherwise, all technical and scientific terms used herein have the same meaning as commonly understood to one of ordinary skill in the art.

A number of materials suitable for use as substrates in the present invention have been described in the art. Particular suitable materials for use as substrates in the present invention include any type of porous substrates known in the art. More particular suitable materials for use as substrates in the present invention include any type of solid porous substrates known in the art.

Accordingly, in one embodiment of the present invention a method is provided, wherein the substrate is a porous substrate.

The substrate may be in the form of beads, particles, sheets, films or membranes and may be permeable. For example, the substrate may consist of bead or particles (such as conventional solid phase synthesis supports), fibers (such as glass wool or other glass or plastic fibers), glass or plastic capillary tubes, or metal oxide membranes. The porous substrate may be planar or have simple or complex shape. The surface to which the molecule is adhered may be an external surface or an internal surface of the porous substrate. Particularly where the surface is porous, the molecule is likely to be attached to an internal surface. Where the solid surface is porous, various pore sizes may be employed depending upon the nature of the system.

The term "microchannel" as used in the present invention refers to a single pore in the porous substrate. A possibly suitable example of pore size diameter as useful in the present invention ranges from about 10-500 nm, or 50-400 nm, or 100-300 nm, or is for instance about 10 nm, 50 nm, 70 nm, 100 nm, 125 nm, 150 nm, 175 nm, 200 nm, 225 nm, 250 nm, 300 nm, 350 nm or 400 nm. A substrate as useful in the method according to the present invention may comprise for instance about $10^5$-$10^9$, $10^6$-$10^8$ or $10^7$ pores per mm$^2$. These dimensions are not to be construed as limiting the present invention.

The material of the porous substrate may be, for example, a metal, a ceramic metal oxide or an organic polymer. In view of strength and rigidity, a metal or a ceramic metal oxide may be used. Above all, in view of heat resistance and chemicals resistance, a metal oxide may be used. In addition, metal oxides provide a substrate having both a high channel density and a high porosity, allowing high density arrays comprising different first binding substances per unit of the surface for sample application. In addition, metal oxides are highly transparent for visible light. Metal oxides are relatively cheap substrates that do not require the use of any typical microfabrication technology and, that offers an improved control over the liquid distribution over the surface of the support, such as electrochemically manufactured metal oxide membrane. Metal oxide membranes having through-going, oriented channels can be manufactured through electrochemical etching of a metal sheet.

Accordingly, in one embodiment of the present invention a method is provided as described herein, wherein said porous substrate is a metallo-oxide substrate.

The kind of metal oxide is not especially limited. As a metal, for example, a porous substrate of stainless steel (sintered metal) can be used. For applications not requiring heat resistance, a porous substrate of an organic polymer can also be used if it is rigid.

Metal oxides considered are, among others, oxides of zirconium, silicium, mullite, cordierite, titanium, zeolite or zeolite analog, tantalum, and aluminum, as well as alloys of two or more metal oxides and doped metal oxides and alloys containing metal oxides.

In one embodiment, a method as described herein is provided wherein said porous substrate is an aluminum-oxide substrate.

The metal oxide membranes are for instance transparent, especially if wet, which allows for assays using various optical techniques. Such membranes have oriented through-going channels with well-controlled diameter and useful chemical surface properties. WO 99/02266 which discloses the use of Anopore™ as a porous substrate which is exemplary in this respect, and is specifically incorporated in the present invention.

The porous nature of the substrate facilitates the pressurized movement of fluid, e.g. the sample solution, through its structure. In contrast to two-dimensional substrates, the flow-through nature of a 3-dimensional substrate or microarray, as employed in the methods as described herein, gives significantly reduced hybridization times and increased signal and signal-to-noise ratios. Further, a positive or negative pressure may be applied to the arrays in order to pump the sample solution dynamically up and down through the substrate pores.

The terms "molecular reaction processes" and "reaction" are used interchangeably throughout the present specification and refer to reaction process involving at least two molecules. Molecular reaction processes as used in the present specification include reactions that are conducted in solution such as, for example, chemical, biological, biochemical, and molecular biological reactions.

Accordingly, in one embodiment a method is provided wherein said molecular reaction is chosen from the group comprising chemical and biochemical reactions.

Suitable examples of reactions to be performed using the methods according to the present specification include, without limitation, isolation of RNA, chromosomal DNA or DNA from plasmids or other vectors, restriction enzyme digestion of nucleic acids, sequencing of nucleic acids, elongation and polymerization of nucleic acids by enzymes, oligonucleotide synthesis, screening of bacterial strains for biologically active clones etc.

Accordingly, in a further embodiment a method as described is provided, wherein said molecular reaction is selected from the group comprising ligation reactions, primer extension reactions, nucleotide sequencing reactions, restriction endonuclease digestions, biological interactions, oligonucleotide synthesis reactions, polynucleotide hybridization reactions, peptide synthesis, and protein binding reactions.

Particular suitable examples of reactions which may be performed according to the present invention, and as exemplified in the present description, include sequence-by-synthesis reactions. Sequencing-by-synthesis reactions are well known in the art, e.g. pyrosequencing.

Accordingly, in one embodiment a method is provided wherein said molecular reaction is a nucleotide sequencing reaction.

In a further embodiment, a method is provided wherein said sequencing reaction is a sequencing-by-synthesis reaction.

An advantage of the present invention is that current protocols may be significantly speeded-up because of the flow-through character of the substrate wherein the reactions take place. Reaction compositions and/or protocols may be simplified by abolishment of enzymatic degradation steps. A method according to the present invention allows for instance a pyrosequencing reaction without the requirement of a nucleotide degradation step by apyrase.

A positive or negative pressure may be applied to the arrays in order to pump the reaction solution dynamically up or down through the substrate pores. Alternatively, the substrates may be subjected to a gravitational force or centrifugal force. The duration, type and strength of the force applied will determine the level of displacement of reaction components within the substrate. An advantage of the present invention is that reaction components may be displaced or refreshed by simple flowing off.

In one embodiment of the present invention, removal of analyte and/or reaction components is by a means selected from the group comprising gravitational force, centrifugal force, pressure, and suction including vacuum.

In one embodiment of the present invention, first reaction components are arrayed on a substrate to form a microarray.

The terms "spot" and "predefined region" are used interchangeably throughout the present invention and relate to individually, spatially addressable positions on the substrate to form an array.

For a given substrate size, the upper limit of number of spots on a substrate is determined by the ability to create and detect spots in the array. The preferred number of spots on an array generally depends on the particular use to which the array is to be put. For example, sequencing by hybridization will generally require large arrays, while mutation detection may require only a small array. In general, arrays contain from 2 to $10^5$ spots and more, or from about 100 to about $10^5$ spots, or from about 400 to about $10^4$ spots, or between about 500 and about 2000 spots, or between 100 and 500 spots, including the outer limits.

In a further embodiment of the present invention said microarray comprises up to 25 spots per mm$^2$.

The expression "first reaction components" as used in the present invention refer to one of the reaction components which is present within predefined regions on the substrate. It will be evident that the first reaction components present within a predefined region does not intermix with first reaction components present within another predefined region. A first reaction component may be attached to said substrate, e.g. covalent, non-covalent or absorptive, or may not be attached to the substrate but kept, e.g. in solution, within the predefined regions.

In one embodiment according to the present invention said first reaction component is chosen from the group comprising protein, polypeptide, peptide, nucleic acid, oligonucleotide, polynucleotide, PCR product, and chemical compounds.

In a particular embodiment according to the present invention said first reaction component is an oligonucleotide.

In a further embodiment according to the present invention said first reaction component is bound to said micro-channel by a mechanism chosen from the group comprising covalent binding, non-covalent binding and absorption.

In a convenient embodiment of the present invention said first reaction component is covalently bound to said micro-channel.

The terms "covalent" and "non-covalent" bond are further explained in the following examples. For cDNA arrays, cDNA clones are amplified by PCR and arrayed onto microscope slides which have been pre-coated with poly-L-lysine. This forms a stable but an essentially non-covalent bond between the oligonucleotide and the slide surface. Alternatively the PCR products can be amino-modified at one of the 5'-termini by using a 5'-amino-modified primer in the PCR. The 5'-amino-modified PCR products can be arrayed onto microscope slides which has been derivatised with an aldehyde functional group. The covalent bond is formed between the amino group on the cDNAs and the aldehyde group on the glass slides to give a permanent attachment of DNA sample to the glass.

In order to effect covalent attachment, in general the substrate will first be activated, i. e. treated so as to create reactive groups on or within the substrate that can react with the first reaction component, e.g a capture polynucleotide, to form a covalent linkage. Those of skill in the art will recognize that the desired reactive group will depend on the chemistry used to attach the first reaction component, e.g the capture polynucleotide, to the porous substrate and the composition of the porous substrate. Typical reactive groups useful for effecting covalent attachment of the capture polynucleotide to the porous substrate include hydroxyl (—OH), sulfonyl (—SH), amino (—NH$_2$), epoxy and carboxyl (—COOH) groups; however, other reactive groups as well will be apparent to those having skill may also be used and are also included within the scope of the invention. A variety of techniques for generating appropriate densities or surface concentrations of reactive groups on myriad types of substrate materials are known in the art, and include, for example chemical activation, corona discharge activation, flame treatment activation, gas plasma activation and plasma enhanced chemical vapor deposition (PECUD). Any of these techniques can be used to activate the porous substrates of the invention, provided that a sufficient density or surface concentration of reactive groups is achieved. Concentrations of reactive groups achieved via any mode of activation can be determined using standard methods for the particular group generated. For example, the activated porous substrates can be reacted with a reporter moiety that provides a quantifiable signal. Non-limiting examples include moieties that bear a radioactive label, moieties that bear a fluorescence label and moieties that, when cleaved from the substrate, can be conveniently quantified using conventional spectroscopic techniques, such as, for example, fluorescence and/or absorbance spectroscopy.

A particular suitable example of covalent immobilization comprises a silanation step as well known in the art. Reference is for instance made to the technology described in WO 01/12846 in this respect.

In another convenient embodiment of the present invention said first reaction component is bound to said micro-channel by absorption.

The terms "analyte" and "analyte molecule" are used interchangeably throughout the present invention. The term "analyte in a sample" refers to a molecule in a sample, i.e. a molecule to be analysed by reaction with reagents provided within and/or to the substrate in which said reaction takes place. Said sample may be any type of sample known in the art.

An analyte as used in the present specification refers to any molecule which may be specifically retained by a target molecule immobilized onto a porous substrate for the purpose of performing micro-array based molecular reaction.

Accordingly, in one embodiment of the present invention an analyte is retained by specific hybridization with a first reaction component.

The term analyte as used in the present specification refers both to separate molecules and to portions of molecules such as e.g. an epitope of a protein. Non-limiting examples of analytes which may be employed in the present invention include, but are not limited to, antibodies including monoclonal antibodies polyclonal antibodies, purified antibodies, synthetic antibodies, antisera reactive with specific antigenic determinants (such as viruses, cells or other materials), proteins, peptides, polypeptides, enzyme binding sites, cell membrane receptors, lipids, proteolipids, drugs, polynucleotides, oligonucleoties, sugars, polysaccharides, cells, cellular membranes and organelles, nucleic acids including deoxyribonucleic acids (DNA), ribonucleic acids (RNA), and peptide nucleic acids (PNA) or any combination thereof; cofactors, lectins, metabolites, enzyme substrates, metal ions and metal chelates.

In a particular embodiment of the present invention said analyte is a nucleic acid.

Subsequent to the specific retaining of an analyte within the substrate, reaction reagents may be added to initiate a molecular reaction process. According to the process envisaged, a single second reaction component may be added but additional reaction components may be included as well. As such a second reaction component may be a reagent mix comprising enzymes or substrates or any mixture thereof. The method according to the present invention allows the sequential addition of at least one second reaction component. At each subsequent addition, the composition of said at least one second reaction component may be changed; e.g. in fill-in, extension and sequencing-by-synthesis reactions wherein different nucleotide species are sequentially added to the reaction.

Accordingly, in one embodiment a method is provided wherein a second reaction component is selected from the group comprising enzymes and enzyme substrates.

In a further embodiment, said second reaction component is an enzyme.

In yet a further embodiment, said enzyme is a DNA/RNA modifying enzyme or a protein tool.

Useful DNA/RNA mofifying enzymes include, by way of example and not limitation, restriction endonucleases, nicking endonucleases, homing endonucleases, DNA polymerases, methylases, ligases, nucleases, Rnases, DNA repair proteins, recombinases, and transposases. Useful protein tools include, by way of example and not limitation, proteases, endoglycosidases, exoglycosidases, protein kinases, protein phosphatases, and inhibitors.

In a particular embodiment of the present invention said modifying enzyme is chosen from the group comprising polymerase, ligases, and nucleases.

In another embodiment of the present invention said second reaction component is an enzyme substrate.

Monitoring of the reaction processes within the substrate is by signals generated by said reactions. Said signals may be transient, i.e. passing especially quickly into and out of existence. The term "transient signal" as used in the present invention refers to e.g. a pulse. In the present invention, each sequential addition of at least one second reaction component is monitored for the generation of a signal pulse. The level and intensity of said pulse may be directly linked to the reaction result upon addition of said at least one second reaction component.

Accordingly, in one embodiment a method is provided wherein said signal is transient.

Signal detection may be a quantitative or a qualitative observation or both.

In one embodiment of the present invention, a method as described herein is provided wherein said signal is by optical radiation.

As used herein, the term "optical radiation" can include radiation that can be used to transmit signals, such as radiation in the visible, ultraviolet, infrared and/or other portions of the electromagnetic radiation spectrum.

Although the embodiments described herein refer to chemi-luminescence, it will be understood that reactions performed according to the present invention may be monitored by for example bioluminescence, radioactive radiation, and fluorescence.

In a convenient embodiment of the present invention a method is provided wherein said optical radiation is chemiluminescence.

Detection methods of the generated signals are well known in the art. Signals may be detected or visualized in a variety of ways, with the particular manner of detection being chosen based on the reporter system which is utilized. Representative detection means include scintillation counting, auto-radiography, optical detection such as fluorescence measurement, colorimetric measurement, light scattering, and the like.

In one embodiment, a method of the invention is described wherein said detection is an optical detection.

In one embodiment, a method of the invention is described wherein said detection is chemi-luminescent light detection.

The term "chemiluminescence" refers to the generation of electromagnetic radiation as light by the release of energy from a chemical reaction. While the light can, in principle, be emitted in the ultraviolet, visible or infrared region, those emitting visible light are the most common. They are also the most interesting and useful.

Chemiluminescent reactions can be grouped into three types:
 1. Chemical reactions using synthetic compounds and usually involving a highly oxidized species such as a peroxide are commonly termed chemiluminescent reactions.
 2. Light-emitting reactions arising from a living organism, such as the firefly or jellyfish, are commonly termed bioluminescent reactions.
 3. Light-emitting reactions which take place by the use of electrical current are designated electrochemiluminescent reactions.

Chemiluminescent and bioluminescent reactions usually involve the cleavage or fragmentation of the O—O bond an organic peroxide compound. Peroxides, especially cyclic peroxides, are prevalent in light emitting reactions because the relatively weak peroxide bond is easily cleaved and the resulting molecular reorganization liberates a large amount of energy In one embodiment of the present invention, a method is provided wherein monitoring of signals generated by the reaction processes is by optical means.

In a further embodiment, said optical means is a CCD imaging system.

In yet a further embodiment of the present invention, monitoring of the reaction processes according to the present invention is in real-time.

In a further embodiment, a method is provided wherein more than one substrate is used simultaneously.

In a further embodiment, a method is provided wherein said more than one substrate is held in one plane by a holding means.

In a further embodiment, a method is provided wherein said holding means is a microtiter plate, said microtiter plate provided with a plurality of separate wells, each well having an inlet opening, a bottom outlet, and a fitting for holding said substrate.

In a further embodiment, the use of a method for high through-put performing and monitoring of molecular reaction processes is provided.

In a further embodiment, the use of a method for monitoring real-time molecular reaction processes is provided.

In a further embodiment, the use of a method for nucleotide sequencing reactions is provided.

In a further embodiment, the use of a method for sequencing-by-synthesis reactions is provided.

In a further embodiment, a microarray for performing a method comprising a substrate having micro-channels, said micro-channels comprising inlet and outlet open ends at opposing sides of said substrate, wherein each micro-channel comprises at least one reaction component selected from the group comprising nucleic acids, enzymes and enzyme substrates is provided.

In a further embodiment, the use of a micro-array for the manufacture of a molecular reaction kit for performing a method according to the present invention is provided.

In a further embodiment, a molecular reaction kit comprising (a) a microarray according to the present invention, comprising first reaction component(s) within the micro-channels, and (b) second reaction component(s), said second reaction component(s) being different from said first reaction components as defined in step (a) is provided.

SHORT DESCRIPTION OF THE FIGURES

FIG. 1A illustrates the results obtained with a substrate onto which a negative control probe was spotted;

FIG. 1B illustrates the results obtained with a substrate onto which 16 pyrosequencing probes were spotted;

FIG. 1C illustrates the results obtained with a substrate onto which one pyrosequencing probe was spotted;

FIG. 1D illustrates the results obtained with a substrate onto which a pyrosequencing probe was spotted;

FIG. 2A illustrates the results obtained with a substrate onto which a pyrosequencing probe was spotted;

FIG. 2B illustrates the results obtained with a substrate onto which probe was spotted; a positive control probe was added;

FIG. 2C illustrates the results obtained with a powder substrate to which a positive control probe was added;

FIG. 2D illustrates the results obtained with a substrate onto which a probe was coupled and to which a positive control probe was added.

FIG. 6A demonstrates the results of a Klenow reaction performed on hybridized plasmid. The analysis was performed in duplicate indicated by reference numbers 1 and 2.

FIG. 6B demonstrates the results of a Klenow reaction performed on non-hybridized plasmid. The analysis was performed in duplicate indicated by reference numbers 1 and 2.

FIG. 7A demonstrates the results obtained after 1 minute of reaction at 55° C. No template was present.

FIG. 7B demonstrates the results obtained after 30 minutes of reaction at 55° C. in the presence of template.

FIG. 7C demonstrates a control experiment performed with Klenow in the absence of template.

EXAMPLES

Example 1

Pyrosequencing of Viral RNA Samples

Introduction

HIV-1 RNA from plasma samples from HIV-1-infected individuals stored at −70° C. are extracted using the NucliSens RNA extraction kit (BioMerieux) according to the manufacturers instructions. The samples are quantified by means of NucliSens HIV-QT (BioMerieux) according to the manufacturers instructions. cDNA is synthesized from the viral RNA by use of a cDNA synthesis kit (Amersham Pharmacia Biotech, Uppsala, Sweden).

Sequence analysis is compared to the Sanger sequencing reaction (Amersham Pharmacia Biotech).

The sequencing reaction is performed on a set of 10 degenerative primers adjacent to a variability sequence region (http://hiv-web.lanl.gov). Primers are spotted and covalently coupled onto the substrate as well known in the art. The cDNA is captured on the array of primers.

Real-time sequencing is performed at 28° C. in a total volume of 10 µl in a substrate incubator. After addition of a first dNTP-triphosphate/enzyme mixture the solution is passed through the substrate by means of a vacuum and the chemiluminescence is recorded by a CCD imaging system (Olympus). Subsequently, 5 µl of cleaning solution is added and passed through the substrate. A next subsequent dNTP-triphosphate/enzyme mixture is added and passed through the substrate and the chemiluminscence is recorded. The latter two steps are repeated.

An advantage over the standard Pyrosequencing process (Pyrosequencing SQA kit, Pyrosequencing AB, Uppsala, Sweden) is a much shorter reaction time since no enzyme or nucleotide degradation steps in between the reactions take place; i.e. the non-incorporated nucleotides are simply and quickly displaced by a flow-through wash step.

Results

Oligonucleotide probes were coupled to small weighed disks of aluminium oxide Anopore substrate ("Anodisc 25", Whatman).

As a positive control oligo, JD-APC-gen #01-0432 (TAATTTTTAGGGTTCAACT—SEQ ID NO. 1) was used; as a negative controle oligo, reverse complementary Thr3 oligo #01-316 (GCGCCATGTCTATTGGACTAGATGGT-TCACCGATTTGCCTGGCGT CTAAA—SEQ ID NO. 2) was used (Fakhrai-Rad, H et al., Human Mutation, Vol. 19 (5), 2002)

In addition, "bare" Anopore membranes (in a disk format or as Anopore powder) were used as true negative controls.

The prepared samples were subsequently tested in the pyrosequencing reaction with the addition of a complementary probe sequence to JD-APC-gen on the PSQ96 system according to the manufacturers package insert. On samples F, G, H as a positive control JD-APC-gen probe was added.

Example 2

Ligation (Fill-in) Reactions

Figure 1:
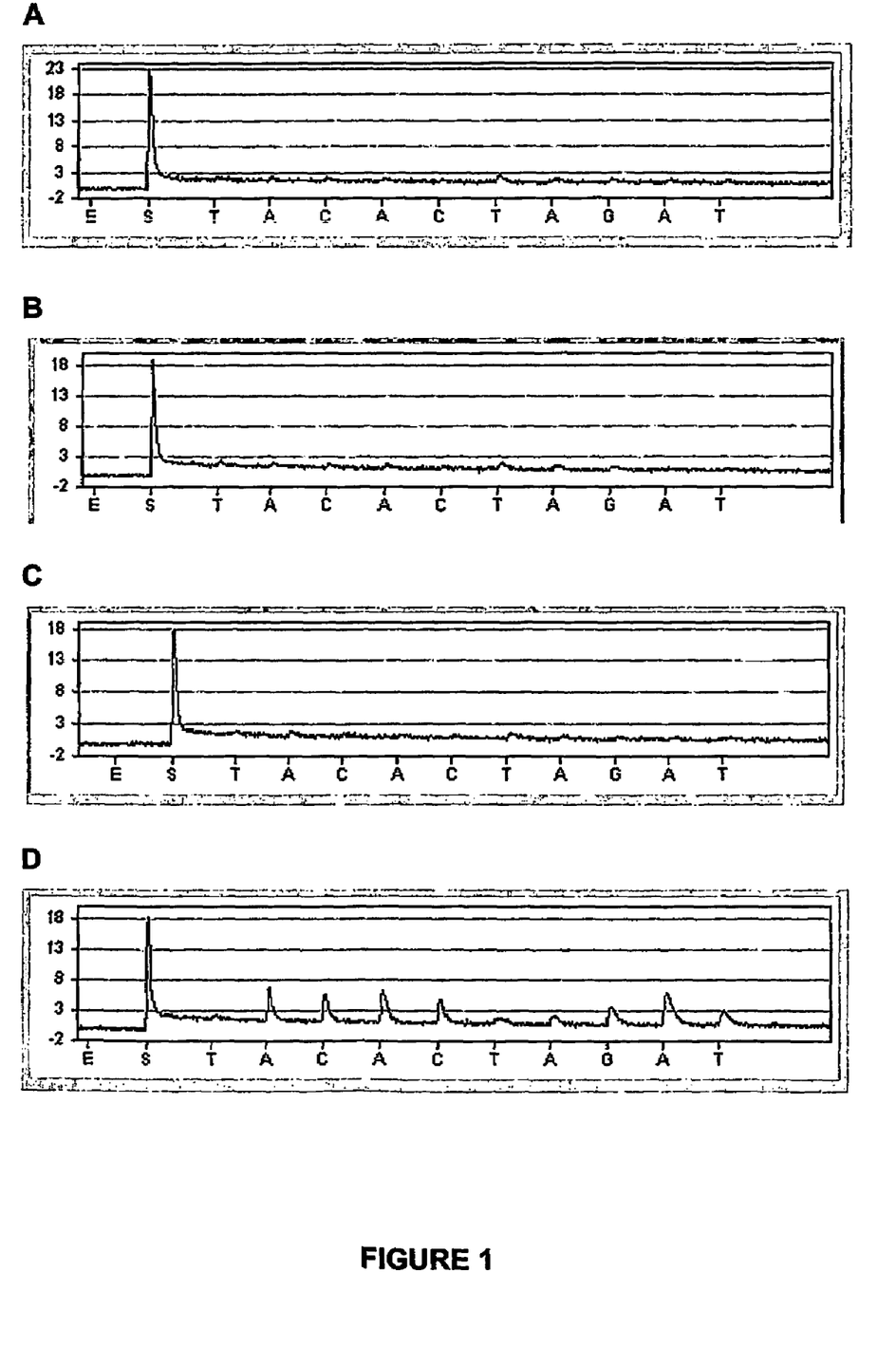
FIG. 1 illustrates the results obtained from a sequencing experiment (see Example 1)
Figure 2:
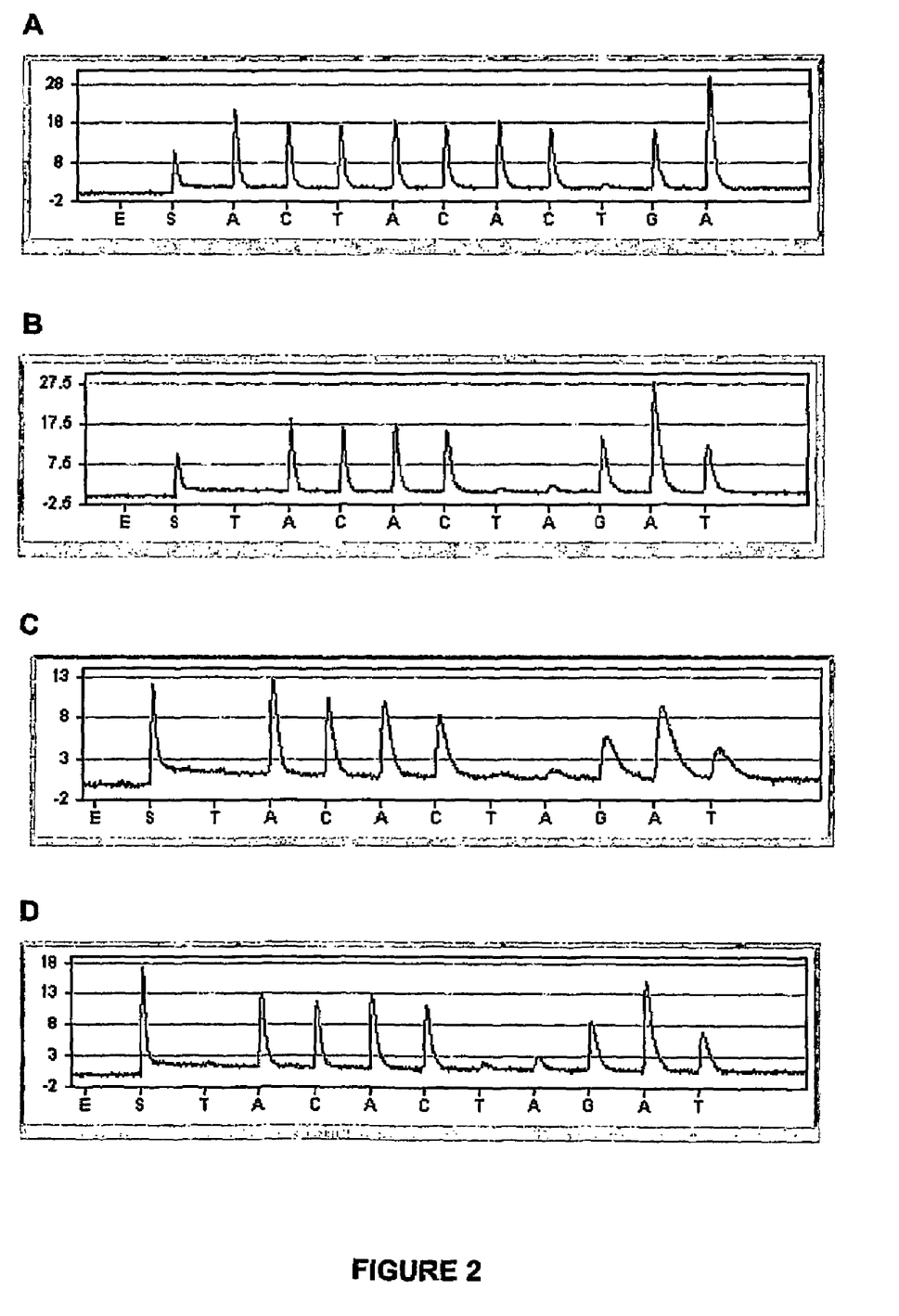
FIG. 2 illustrates the results obtained from a sequencing experiment (see Example 1)
Figure 3:
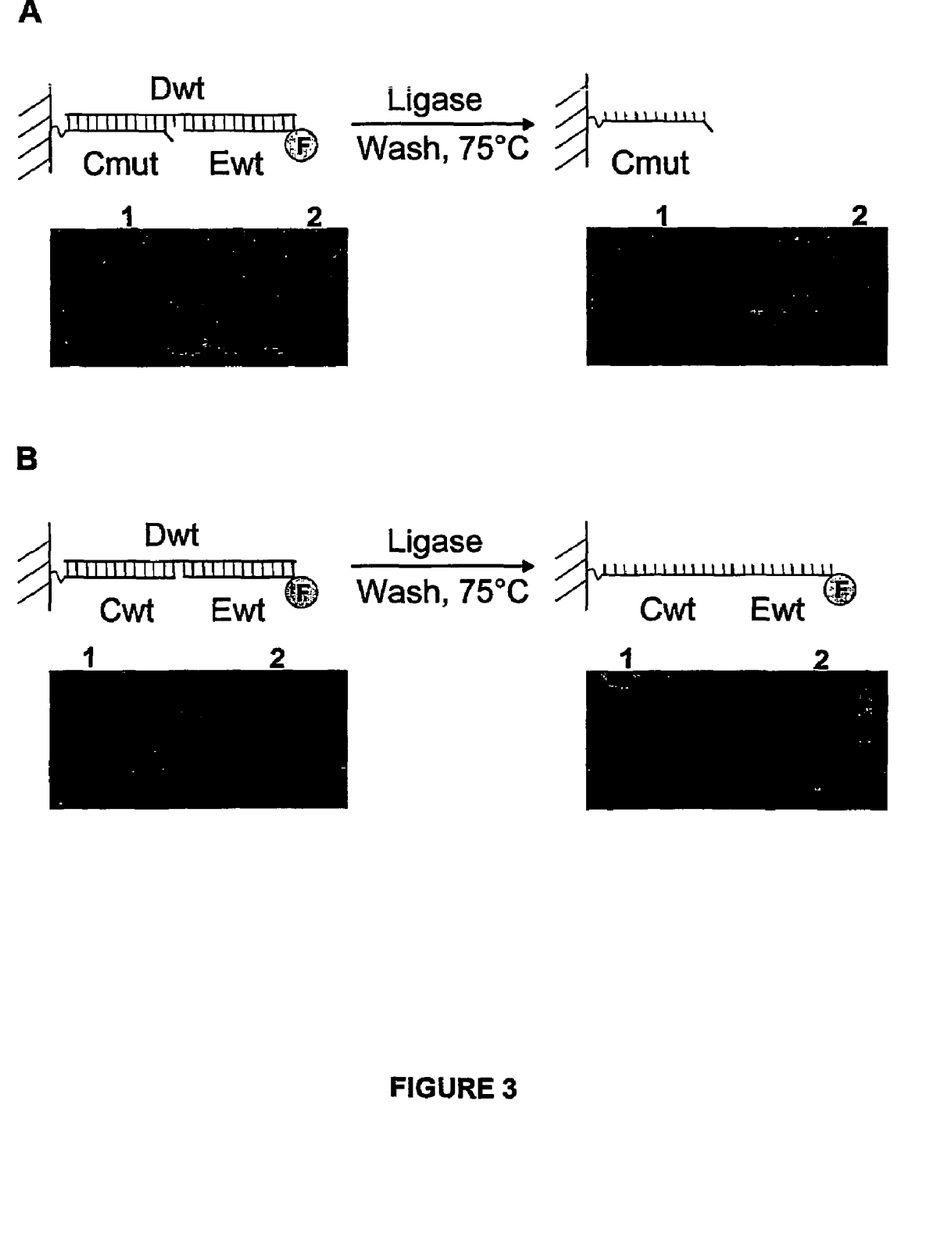
FIG. 3 illustrates a first and second ligation reaction as described in Example 2.
Figure 4:
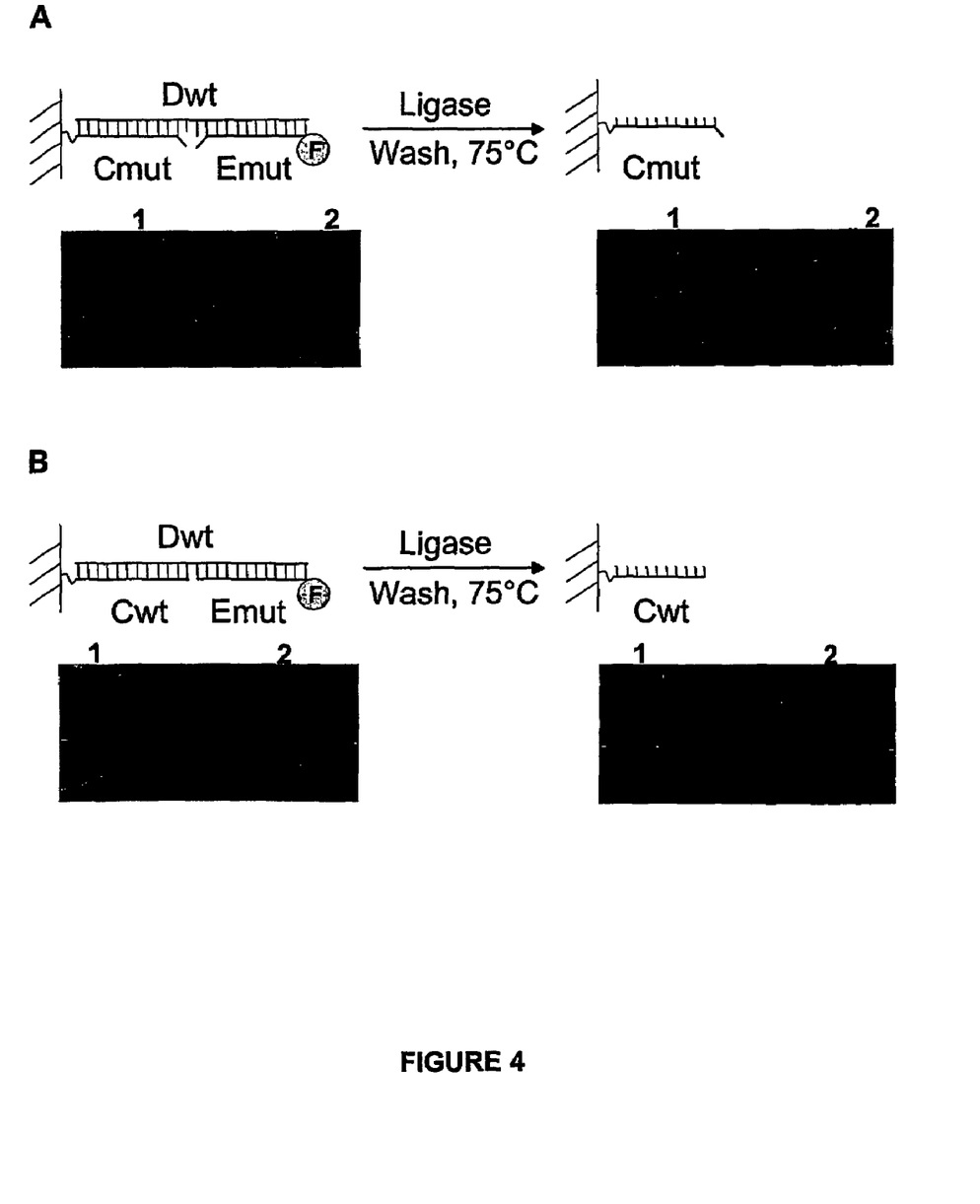
FIG. 4 illustrates a third and fourth ligation reaction as described in Example 2.

Arrays, on which wild-type (wt) and mutant (mut) forms of a fragment C were spotted, were hybridized with 1 nM of wild type fragments D (Dwt) and subsequently hybridized with respectively wild type fragments E (Ewt) or mutant fragments E (Emut) in 20 µl 6×SSPE (Sodium chloride Sodium Phosphate-EDTA)/5×Denhardt for 1 hour at room temperature. Subsequently the arrays were washed with 2×SSPE at room temperature. Then 20 µl ligase mix (10 units T4 ligase, Promega) in ligase buffer was added and ligation took place for two hours at room temperature while pumping the reaction mix up and down through the pores of the substrate. Subsequently, the membrane was washed with water at 75° C. for 5 minutes and images were taken. Each analysis was done in duplicate ("1" and "2" as shown in FIG. 3 and FIG. 4).

In a first experiment (A, FIG. 3), a mutant fragment Cmut is coupled to the substrate. A template wild type fragment Dwt is hybridized to Cmut as well as a wild type fragment Ewt. Because fragment C is mutated, said fragment cannot be ligated to Ewt with Dwt serving as a template. Accordingly, no signal is detected upon analysis of the ligation reaction after ligation and washing was performed.

In a second experiment (B, FIG. 3), a wild type fragment Cwt is coupled to the substrate. A template wild type fragment Dwt is hybridized to Cwt as well as a wild type fragment Ewt. Because fragments C and E are wild type, said fragments were ligated with Dwt serving as a template. Accordingly, signal was detected upon analysis of the ligation reaction after ligation and washing was performed.

In a third experiment (A, FIG. 3), a mutant fragment Cmut is coupled to the substrate. A template wild type fragment Dwt is hybridized to Cmut as well as a mutant fragment Emut. Because both fragments C and E are mutated, said fragments cannot be ligated with Dwt serving as a template. Accordingly, no signal was detected upon analysis of the ligation reaction after ligation and washing was performed.

In a fourth experiment (B, FIG. 4) a wild type fragment Cwt is coupled to the substrate. A template wild type fragment Dwt is hybridized to Cwt as well as a mutant fragment Emut. Because fragment E is mutant, said fragment cannot be ligated to Cwt with Dwt serving as a template. Accordingly, no signal was detected upon analysis of the ligation reaction after ligation and washing was performed.

Example 3

Klenow and Taq Reactions

Figure 5:
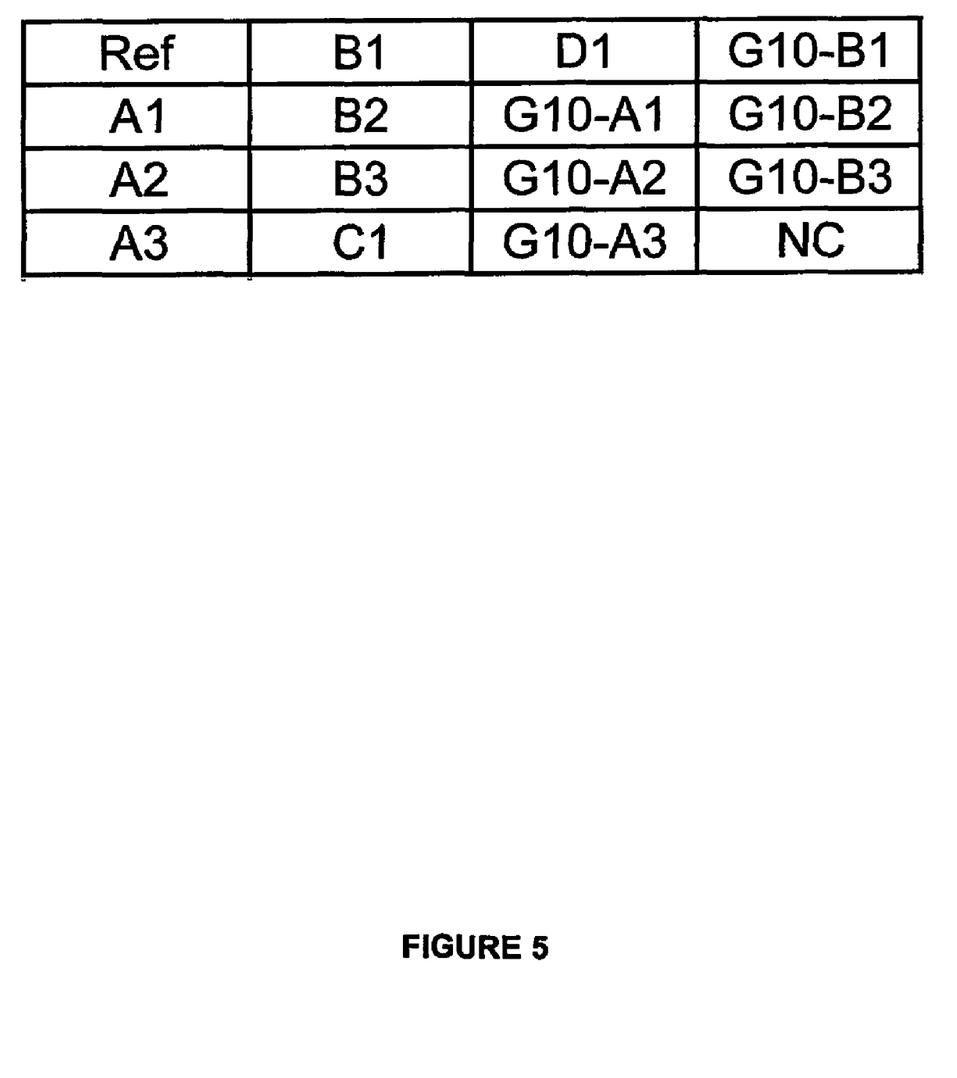
FIG. 5 illustrates the lay-out of the array as used in Example 3.
Figure 6:
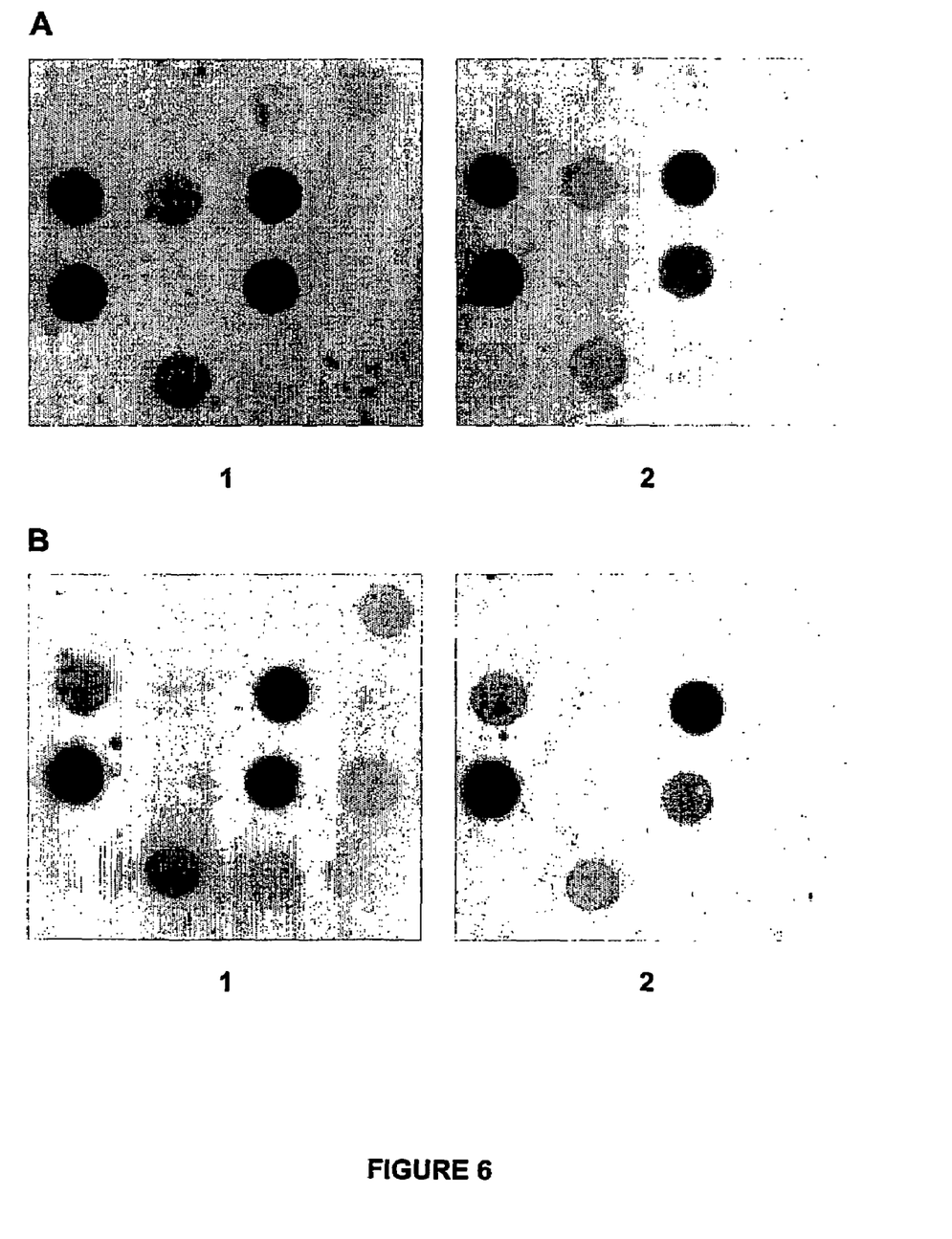
FIG. 6 illustrates the results obtained from the Klenow reaction as described in Example 3.
Figure 7:
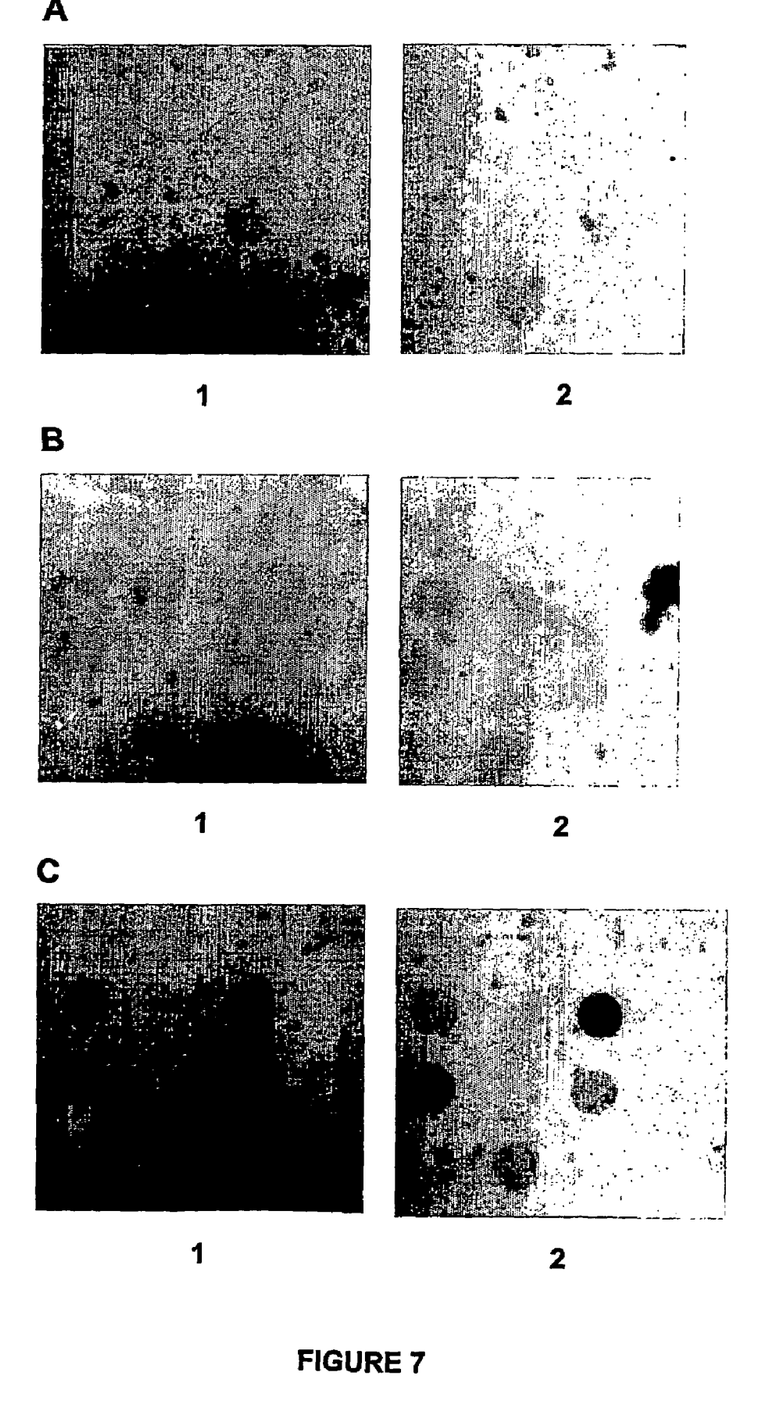
FIG. 7 illustrates the results from a Taq-polymerase reaction as described in Example 3.

Metal oxide substrates were hybridized with denatured plasmid pGEM-luciferase under standard conditions. The array lay-out is as shown in FIG. 5. This membrane and a control membrane were washed and incubated with Klenow enzyme (FIG. 6) at room temperature for 30 minutes or with Taq.polymerase (FIG. 7) at 95° C. for 1 minute and for 30 minutes at 72° C. in a standard nick-translation buffer containing 10% fluorecein-UTP. Afterwards the membranes were washed in water at 95° C. for 5 minutes. Each experiment was performed in duplicate (as indicated by "1" and "2" in FIGS. 6 and 7).

TABLE 1

| # | Anopore mg | Surface ($cm^2$) | Description |
|---|---|---|---|
| A | 0.41 | 0.052 | Anopore disk coupled with negative control probe (01-0316) whole surface activated |
| B | 0.43 | 0.055 | Anopore disk coupled with positive control probe (01-0432) 13% of surface activated |
| C | 0.43 | 0.055 | Anopore disk coupled with positive control probe (01-0432) 1% of surface activated |
| D | 0.52 | 0.066 | Anopore disk coupled with positive control probe (01-0432) whole surface activated |
| E | NA | | Positive control in Pyrosequencing PSQ96 |
| F | 0.46 | 0.059 | Anopore disk bare with addition of positive control probe (01-0432) in solution |
| G | 15.96 | 2.03 | Anopore powder with addition of positive control probe in solution |
| H | 0.45 | 0.057 | Anopore disk coupled with positive control probe (01-0432) whole surface activated and with addition of control probe in solution |

The invention claimed is:

1. A method for monitoring in a high through-put fashion a multitude of molecular reaction processes, using a substrate, said substrate comprising a plurality of micro-channels, wherein each micro-channel has inlet and outlet open ends on opposing sides of said substrate, and wherein said micro-channels comprise at least one first reaction component, comprising the steps of:
   (a) contacting said micro-channels of said solid substrate with a sample, said contacting being via said inlet open ends, wherein said sample comprises an analyte, under conditions that allow said analyte to be specifically retained within said micro-channels by said first reaction component;
   (b) optionally removing excess of sample via said outlet open ends;
   (c) contacting the retained analyte with at least one second reaction component, said second reaction component being different from said first reaction component as defined in step (a), under conditions that allow a molecular reaction to take place, said reaction producing a signal;
   (d) detecting said signal and reading-out reaction results;
   (e) removing second reaction components via said outlet open ends;
   (f) repeating steps (c) to (e) at least once, wherein said at least one secondreaction component as defined in (c) may be changed in composition; and,
   (g) final detecting and reading-out of reaction results.

2. The method according to claim 1, wherein said substrate is a porous substrate.

3. The method according to claim 1, wherein said substrate is a metallo-oxide substrate.

4. The method according to claim 3, wherein said metallo-oxide substrate is an aluminum-oxide substrate.

5. The method according to claim 1, wherein said first reaction components are arrayed on the substrate to form a microarray.

6. The method according to claim 5, wherein said microarray comprises up to 25 spots per $mm^2$.

7. The method according to claim 1, wherein said first reaction component is chosen from the group consisting of a protein, a polypeptide, a peptide, a nucleic acid, an oligonucleotide, a polynucleotide, a PCR product, and chemical compounds.

8. The method according to claim 1, wherein said first reaction component is bound to said micro-channel by a mechanism chosen from the group comprising covalent binding, non-covalent binding and absorption.

9. The method according to claim 1, wherein said analyte is a nucleic acid.

10. The method according to claim 1, wherein a target is retained by specific hybridization with said first reaction component.

11. The A method according to claim 1, wherein said second reaction component is an enzymes or enzyme substrates.

12. The method according to claim 11, wherein said enzyme is a DNA/RNA modifying enzyme or a protein tool.

13. The method according to claim 12, wherein said modifying enzyme is chosen from the group comprising polymerase, ligases, and nucleases.

14. The method according to claim 1, wherein said removal of sample and/or second reaction components is by a means selected from the group consisting of gravitational force, centrifugal force, pressure, and suction including vacuum.

15. The method according to claim 1, wherein said molecular reaction is a chemical reaction or a biochemical reaction.

16. The method according to claim 15, wherein said molecular reaction is selected from the group comprising of a ligation reaction, a primer extension reaction, a nucleotide sequencing reaction, a restriction endonuclease digestion, a biological interaction, an oligonucleotide synthesis reaction, polynucleotide hybridization reactions, peptide synthesis, and protein binding reactions.

17. The method according to claim 16, wherein said nucleotide sequencing reaction is a sequencing-by-synthesis reaction.

18. The method according to claim 1, wherein said signal is transient.

19. The method according to claim 18, wherein said signal is by optical radiation.

20. The method according to claim 19, wherein said optical radiation is chemi-luminescence.

21. The method according to claim 1, wherein said detection is an optical detection.

22. The method according to claim 21, wherein said detection is chemi-luminescent light detection.

23. The method according to claim 1, wherein said monitoring is by optical means.

24. The method according to claim 23, wherein said optical means is a CCD imaging system.

25. The method according to claim 1, wherein said monitoring is in real-time.

* * * * *